US011033597B2

(12) United States Patent
Hendriks

(10) Patent No.: US 11,033,597 B2
(45) Date of Patent: Jun. 15, 2021

(54) DERMATOLOGICAL KIT COMPRISING COMPOSITIONS BASED ON HIBISCUS FLOWER AND BURITI OIL

(71) Applicant: MEDICAL BRANDS RESEARCH B.V., Amsterdam (NL)

(72) Inventor: Maikel Hendriks, Amsterdam (NL)

(73) Assignee: MEDICAL BRANDS RESEARCH B.V., Amsterdam (NL)

( * ) Notice: Subject to any disclaimer, the term of this patent is extended or adjusted under 35 U.S.C. 154(b) by 750 days.

(21) Appl. No.: 15/516,920

(22) PCT Filed: Oct. 6, 2015

(86) PCT No.: PCT/EP2015/072982
§ 371 (c)(1),
(2) Date: Apr. 5, 2017

(87) PCT Pub. No.: WO2016/055440
PCT Pub. Date: Apr. 14, 2016

(65) Prior Publication Data
US 2017/0296613 A1 Oct. 19, 2017

(30) Foreign Application Priority Data

Oct. 6, 2014 (EP) .................................... 14187814

(51) Int. Cl.
| *A61K 36/889* | (2006.01) |
| *A61K 8/36* | (2006.01) |
| *A61Q 19/02* | (2006.01) |
| *A61Q 19/08* | (2006.01) |
| *A61K 36/185* | (2006.01) |
| *A61K 31/194* | (2006.01) |
| *A61K 31/352* | (2006.01) |
| *A61K 31/375* | (2006.01) |
| *A61K 31/51* | (2006.01) |
| *A61K 31/525* | (2006.01) |
| *A61K 31/085* | (2006.01) |
| *A61K 8/9789* | (2017.01) |
| *A61K 31/19* | (2006.01) |
| *A61K 9/00* | (2006.01) |

(52) U.S. Cl.
CPC .............. *A61K 36/889* (2013.01); *A61K 8/36* (2013.01); *A61K 8/9789* (2017.08); *A61K 9/0014* (2013.01); *A61K 31/085* (2013.01); *A61K 31/19* (2013.01); *A61K 31/194* (2013.01); *A61K 31/352* (2013.01); *A61K 31/375* (2013.01); *A61K 31/51* (2013.01); *A61K 31/525* (2013.01); *A61K 36/185* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 5,804,168 A * | 9/1998 | Murad ................. A61K 8/9771 424/59 |
| 7,794,759 B2 | 9/2010 | Kikuchi et al. |
| 2006/0013786 A1 | 1/2006 | Hanano |
| 2009/0214607 A1 | 8/2009 | Lintner et al. |

FOREIGN PATENT DOCUMENTS

| CN | 101199463 | 6/2008 |
| EP | 2 407 151 | 1/2012 |
| JP | 2006-306863 | 11/2006 |

OTHER PUBLICATIONS

Humphreys, et al., J. Am. Acad. Dermatol., 34:638. (Year: 1996).*
Zanatta, et al., Food and Chemical Toxicology, 48:70. (Year: 2010).*
Translation of WO2006106992A1 (English translation provided by Google Patents). (Year: 2006).*
Translation of BR0303404A Abstract (English translation provided by Google Patents). (Year: 1996).*
CN103108623A translation, retrieved from Google Patents. (Year: 2013).*
International Search Report for PCT/EP2015/072982, dated Jan. 15, 2016, 5 pages.
Written Opinion of the ISA for PCT/EP2015/072982, dated Jan. 15, 2016, 6 pages.
Search Report for EP 14187814, dated Apr. 16, 2015, 4 pages.
Database GNPD [Online] MINTEL, Dec. 2010 (Dec. 2010), "Sunscreen SPF 15", XP002738500.
Database GNPD [Online] MINTEL, Jun. 2014 (Jun. 2014), "Multiplant Sunscreen Lotion SPF38/PA+++", XP002738499.
Smit et al., "The Hunt for NaturalSkin Whitening Agents", International Journal of Molecular Sciences, Molecular Diversity Preservation International, Basel, CH., vol. 10, No. 12., Dec. 10, 2009, (Dec. 10, 2009), pp. 5326-5349, XP002656718.
Fabi et al., Efficacy and tolerability of two commercial hyperpigmentation kits in the treatment of facial hyperpigmentation and photoaging, Journal of Drugs in Dermatology: JDD Aug. 2012, vol. 11. No. 8, Aug. 2012 (Aug. 2012), pp. 964-968, XP002737837.
Brown, "Treating Solar Lentigines: Traditional treatments at a glance—plus, a look at a cutting-edge option.: The Dermatologist", The Dermatologist, Aug. 1, 2002 (Aug. 1, 2002), 2 pages, XP055179719.
Office Action, CN Application No. 201580063528.6, dated Jul. 7, 2020.
Third Office Action, CN Application No. 201580063528.6, dated Feb. 1, 2021.

* cited by examiner

*Primary Examiner* — Michael Barker
(74) *Attorney, Agent, or Firm* — Nixon & Vanderhye P.C.

(57) ABSTRACT

The invention provides a dermatological kit comprising a first container comprising a first composition and a second container comprising a second composition, different from the first composition, wherein the first composition comprises trichloroacetic acid and a hibiscus acid, wherein the second composition comprises a material of *Mauritia flexuosa* origin and a hibiscus acid, and wherein the second composition has a sun protection factor (SPF) of at least 15.

20 Claims, No Drawings

DERMATOLOGICAL KIT COMPRISING COMPOSITIONS BASED ON HIBISCUS FLOWER AND BURITI OIL

This application is the U.S. national phase of International Application No. PCT/EP2015/072982 filed 6 Oct. 2015, which designated the U.S. and claims priority to EP Patent Application No. 14187814.0 filed 6 Oct. 2014, the entire contents of each of which are hereby incorporated by reference.

FIELD OF THE INVENTION

The invention relates to a kit comprising at least two compositions. The invention further relates to such kit for use in the treatment of brown spots.

BACKGROUND OF THE INVENTION

Various compositions for the treatment of skin hyperpigmentation are known in the art. WO 2012/007584, for instance, describes a composition for the treatment of superficial lesions, in particular skin lesions, mucous membrane lesions and/or nail lesions. WO 2012/007584 further describes an applicator comprising such a composition and the use of such a composition. The composition comprises an effective amount of trichloroacetic acid, at least one thickener, and at a physiologically acceptable solvent. And is effective against a plethora of superficial lesions selected from the group consisting of viral warts, verrucae, water warts (molluscum contagiosum), corns and calluses, and skin hyperpigmentation: age spots, solar lentigo, seniallentigo, acne, keratosis pilaris, actinic keratosis, mouth ulcers (canker sores), cold sores, ingrown toenails, onychomycosis, and eyelid xanthelasma.

SUMMARY OF THE INVENTION

A skin is a living organ made up of millions of cells. Everyday thousands of cells die, fall off and are replaced by new cells from below. Unfortunately, as we age, this becomes slower and more haphazard process, making a skin unable to shed abnormalities and small injuries, such as dark blotches and sun damage.

A solar lentigo (plural, solar lentigines), also known as a sun-induced freckle or senile lentigo, hyperpigmentation, age spot, brown spot, liver spot and black spot, is a dark lesion associated with aging and exposure to the sun or to artificial ultraviolet (UV) light. Solar lentigines occur mainly on sun-exposed parts of the body such as the face, neck, décolleté, upper back, arms, hands and feet. They range in color from light brown to dark brown, nonpainful, usually uniform in color, have smooth border and remain stable in appearance. Solar lentigines may be single or multiple. Although solar lentigines most commonly occur in older adults, particularly those who sunburn easily and fail to tan, they may also occur in children.

Various (topical) compositions are known for treatment of brown spot. Many of these compositions have no or only a moderate effect and/or have undesired side effects. Further, many of those compositions include a significant amount of non-natural active components, which may be less desirable to the person using the compositions. Hence, it is an object of the invention to provide an alternative composition, especially a more effective and improved composition. It is further an object of the invention to provide an alternative kit comprising (containers comprising) such composition, for the treatment of skin hyperpigmentation.

For a durable treatment of brown spots it appears to be desired that after removal and/or treatment of the brown spot, the skin is reinforced and protected from harmful UV radiation. The present invention combines this plural constraint in a dermatological kit having multiple functionalities. To this end, the invention provides two (dermatological) compositions. A first composition is especially provided for its peeling functionality. When used on a brown spot, the exfoliating properties of the composition are exploited to treat and steadily remove the brown spot. After application of the first composition the second dermatological composition is provided to the brown spot being treated with the first composition, to support the peeling process, to stimulate the natural cell renewal in the skin and to protect the sensitive skin from harmful UV radiation.

It was found that the material of the *Hibiscus sabdariffa* flower or calyx have advantageous properties, such as one or more of antioxidant properties (and therefore may protect cells against DNA damages), antibacterial properties, and peeling properties. Especially the acid from the *Hibiscus sabdariffa* has gentle but efficient exfoliating properties and stimulates the skin renewal. Hence, the acids of the *Hibiscus sabdariffa*, especially hibiscus acid, are fitting the first composition as well as the second composition. Whereas the hibiscus acids may be supported by a second exfoliating agent like trichloroacetic acid in the first composition, it may be applied as single exfoliating agent in the second composition to induce a less severe but prolonged peeling action. Further, it surprisingly appeared that a combination of trichloroacetic acid and hibiscus acid has advantages in the treatment of brown spots.

It was further surprisingly found that material of *Mauritia flexuosa* origin is capable to filter and absorb UV rays from the sun and provides natural soothing properties to the skin. Hence the material of *Mauritia flexuosa* origin is most appropriate for the second composition to protect the treated skin from UV radiation and to support the healing process.

Therefore, in a first aspect, the invention provides a (dermatological) kit (herein also indicated as "kit") comprising a first container comprising a first (dermatological) composition and a second container comprising a second (dermatological) composition (different from the first composition), wherein the first composition comprises trichloroacetic acid (TCA) and another organic acid, especially wherein the first composition comprises trichloroacetic acid and a hibiscus acid, and wherein the second composition also comprises a hibiscus acid and further a material of *Mauritia flexuosa* origin. Especially, the invention provides a (dermatological) kit comprising a first container comprising a first composition and a second container comprising a second composition, different from the first composition, wherein the first composition comprises trichloroacetic acid and a hibiscus acid, wherein the second composition comprises a material of *Mauritia flexuosa* origin and a hibiscus acid, and wherein the second composition especially has a sun protection factor (SPF) of at least 15, such as at least 20, even more at least 25, such as at least 30, even more at least 50.

The subsequent application of the first composition and the second surprisingly appears to provide a much better effect than the first composition alone, or the second composition alone or the first composition and a state of the art UV-filter (UV filtering material, such as a sun tan).

In yet a further aspect, the invention also provides such (dermatological) kit, especially for use in the treatment and/or prevention of an sun induced skin hyperpigmentation, especially brown spot (solar lentigo), wherein the first composition is especially used to remove and/or fade the hyperpigmentation and wherein the second composition is especially used to remove and/or fade the hyperpigmentation and to prevent the re-development of hyperpigmentation.

In yet a further aspect, the invention also provides such kit, especially for use in the prevention of a sun induced skin hyperpigmentation, especially brown spot, wherein the second composition is used to protect the skin from UV-A and UV-B radiation. Hence, the kit may be used for a medical and/or cosmetical treatment.

Therefore, the invention also provides such (dermatological) kit as defined herein, for use in a method for the treatment of a brown spot, the method comprising: (i) providing the first composition on the brown spot (and allowing the first composition to dry); (ii) providing the second composition to the brown spot (covering the dried first composition); and (iii) repeating step (ii) (allowing the first composition to exfoliate the skin).

In another aspect, the invention also provides the respective compositions per se. In yet a further aspect, the invention also provides such compositions contained by applicators, respectively. Hence, the invention also provides an applicator device comprising the first composition or the second composition as defined herein. The invention also provides a container comprising the first composition or the second composition as defined herein.

DETAILED DESCRIPTION OF THE EMBODIMENTS

Herein the term "hibiscus acid" especially indicates that an acid naturally present in a *Hibiscus* species and/or its naturally present derivative compound(s), especially the ester of the acid and the salt of the acid, is comprised. The term "hibiscus acid" may refer to an acid compound naturally present in any part of a *Hibiscus* species, like leafs, roots, branches. It also may refer to an acid compound naturally present in the flower or calyx of a *Hibiscus* species.

The "hibiscus acid", especially, may be extracted from the flower of the *Hibiscus species*. As indicated below, "hibiscus acid" may specially be present in the flower or calyx of the *Hibiscus sabdariffa*. Especially "hibiscus acid" may refer to (+) hydroxycitric acid and/or (+) hydroxycitric acid lactone (2S,3R-dihydroxy-1,2,3-propanetricarboxylic acid lactone). Hence, in an embodiment hibiscus acid comprises (+) hydroxycitric acid and/or (+) hydroxycitric acid lactone (2S,3R-dihydroxy-1,2,3-propanetricarboxylic acid lactone).

The term "kit" may especially refer to a combination of two or more separate components, i.e. herein especially the compositions, providing the desired effect collectively, though application of the components may be done subsequently. The kit comprises at least two containers each comprising one of the two (dermatological) compositions. The kit, however, is not limited to two containers and two compositions. The kit, e.g., also may comprise one or more applicator devices, or applicators. An applicator (device) is especially a device configured to hold one of the containers containing the composition(s) as described herein and is further especially configured to release part of the composition upon a user action, such as sweeping or pressing a composition access part of the applicator device to the skin, or spraying the composition with a spray applicator device. In a further embodiment, the applicator comprises the container.

Further, the applicator may comprise the container and an application item such as a pen tip, a spray unit, etc. The application item, i.e. an item with which the composition can be applied to the skin, is functionally connected with the container.

Moreover, if more than one applicator is provided in the kit, these applicators may be the same or different for the two different compositions. Also different applicators may be included for the same composition enabling to apply the composition at different locations on a body. Especially, the applicator may comprise a pen ("pen applicator"). Especially the applicator comprising the first composition comprises a pen, and especially the first composition contained by the applicator comprises a gel.

The respective applicator and container may be configured to be detachably connected. In this way, when a container is empty a new container may be functionally connected to the applicator. Note that the kit may optionally include a single applicator, e.g. for the first composition only. The second composition may be contained by the container and may be retrieved therefrom (e.g. a container with a cream).

Herein, the term "dermatological" and similar terms especially relate to the skin. A dermatological composition is a composition that is suitable to be applied to the skin. This term is known to the person skilled in the art. The (dermatological) composition herein may especially be applied for (use in) the treatment and/or prevention of sun induced hyperpigmentation. The (dermatological) composition herein may therefore also be used in a prophylactic treatment.

In a preferred embodiment, the first composition is only applied once or twice at the brown spot, whereas the second composition is applied at least once a day for an extended period, such as weeks, a month, or even more than a month. In a specific embodiment, it therefore may be desirable to have at least one container comprising the first dermatological composition and one or more, especially at least two, containers comprising the second dermatological composition.

Therefore, the invention also provides a method for the treatment of a brown spot according to any of the preceding claims, the method comprising: (i) providing the first composition on the brown spot (and allowing the first composition to dry); (ii) providing the second composition to the brown spot (covering the dried first composition); (iii) repeating step (ii) (and allowing the first composition to exfoliate the skin), wherein in a further specific embodiment the first composition is provided on a first day, and wherein thereafter the second composition is provided on a daily basis during at least two weeks. Optionally, the first composition may be applied a couple of days, and the second composition is applied a couple of weeks. In an embodiment, during a short period, such as a day or a few days, both compositions are applied though in general when applied at the same day, first the first composition is applied and thereafter (after drying) the second composition is applied. Especially, the number in days the first composition is applied will be substantially shorter than the number of days the second composition is applied, such as 2 times, even more especially 5 times, yet even more especially 10 times shorter. Examples are 1 day the first composition and a month the second composition, or two days the first composition, and the second composition a months or two months. Note that the first composition will be applied in general not more than 5 times, such as not more than three times a day, like only once a day (such as in an embodiment only once). The same may apply for the second composition.

Optionally the method comprises washing the brown spot (and/or treated area) with water, and optionally a cleanser (before, after, or between successive steps of the method). Especially, the method may comprise washing the (treated) area/brown spot after providing the first composition to the brown spot and allowing the first composition to dry and/or exfoliate the skin and (the step of) providing the second composition to the brown spot (treated by the first composition). Hence, in an embodiment, the method comprises: (i) providing the first composition on the brown spot, and optionally (after allowing the first composition treat the brown spot) washing (with water) the area being treated with the first composition; (ii) providing the second composition to the brown spot (at least partly covering the area treated with the first composition (and optionally washed)); (iii) repeating step (ii) (and allowing the first composition and/or the second composition to exfoliate the skin), wherein in a further specific embodiment the first composition is provided on a first day, and wherein thereafter the second composition is provided on a daily basis during at least two weeks.

In a further embodiment, the first composition is provided to the brown spot at five consecutive days. Especially, the first composition is allowed to absorb in the skin for a determined period of time (and treat the skin), such as at maximum 10 minutes, such as 5 minutes. After the determined time, the (by the first composition) treated area may be washed with water. After treating the brown spot with the first composition, especially after washing the treated area, the second composition is provided to the treated area. Especially, the treated area is provided (daily) with the second composition for at least 30 consecutive days.

The embodiment of an applicator may depend on the characteristics of the composition(s). For instance for an aqueous composition having a viscosity around 1 mPas a spray applicator may be used, whereas another applicator embodiment will be more appropriate for a composition having a viscosity in the range of about 1,000-250,000 Pas. In an embodiment the kit comprises a pen applicator (herein also indicated as "applicator pen") to hold the first container comprising the first composition. The first composition may in an embodiment be a topical composition, such as a cream, a foam, a gel, a lotion and an ointment. In a specific embodiment, the first composition comprises a gel. Additionally the kit comprises a spray applicator for the second container and the second container comprise the second composition is in an aqueous state. In another embodiment the first composition comprises a gel and the applicator comprising the first composition comprises a pen applicator. Additionally the kit comprises an applicator comprising the second composition, especially comprising a cream.

In yet another embodiment, the spray applicator device may include an aerosol powder spray (applicator device). Other applicator devices may include a roll on applicator, a spatula, a spray applicator including a mask, a pen applicator etc. . . . . Other options may also be possible, like a paste or powder. The pen applicator device may especially be a spot pen (applicator device). Further, the composition may be included in a tube. Hence, also a tube including the composition as described herein is provided.

The first and the second composition may be available in the form of e.g. a liquid, a foam, a cream, paste, powder, etc. Hence, especially the compositions are topical composition, such as a cream, a foam, a gel, a lotion and an ointment, etc. The compositions may be applied in different ways, like e.g. as spray, as cream, as stick, as pen, etc. Further, one of the compositions may also be available as coating or impregnated material in or on a bandage, a patch, a plaster, like an adhesive bandage, or a wound dressing, etc. . . . .

Hence, in an embodiment the first composition comprises a liquid or gel and/or the second composition comprises a lotion, a cream, an ointment, a foam, a paste, or a gel. In a specific embodiment, the first composition comprises a gel. Further, the dermatological kit may comprise a first applicator comprising the first composition, or comprising a second applicator comprising the second composition, or comprising both the first applicator comprising the first composition and the second applicator comprising the second composition. Especially, the first applicator comprises a spray or an applicator pen.

Preferably the viscosity of the first as well as the viscosity of the second composition is at least 1 mPas at 25° C., preferably at least 3,000 mPas. Such compositions have a significant adhering effect on the skin, allowing very local treatment, such as brown spot treatment. Compositions with viscosities up to 60,000 mPas are considered useful. Compositions having viscosities over 100,000 are considered difficult to handle.

In an embodiment, the second composition is a sprayable liquid, having a viscosity in the range of about 1-2,000 mPas. Spraying is a fast and easy way to apply the composition to the surface of the skin using a spray applicator. In another embodiment, the viscosity of the second composition is in the range of about 5,000 mPas-60,000 mPas, and the second composition preferably is a gel composition and is applied to the skin by a spatula. The gel composition is relatively easily to apply, either manually or by a suitable applicator device and comprises a relative large adhering effect.

Preferably the viscosity of the first composition and the viscosity of the second composition is in the range of 450 mPas to 10,000 mPas at 25° C., more preferably the viscosities are ranging from 5,000 to 10,000 mPas at 25° C. Such a composition shows a sufficient adhering effect to the skin, while still being relatively easy to apply and process.

In an embodiment the first composition and the second composition of the (dermatological) kit each comprise one or more phenolic compounds, one or more flavonoid-type polyphenol compounds, one or more organic acid compounds, and one or more vitamin and/or provitamin compounds. Hence, especially the first composition and the second composition each independently comprise a phenolic compound, a flavonoid-type polyphenol compound, an organic acid, and one or more of a vitamin and provitamin.

Different natural compounds may be present in the composition. In an embodiment the first and the second composition may comprise protocatechuic acid and/or eugenol, anthocyanins, anthocyanidins or a glucoside of quercetin. The first and the second composition further may comprise organic acids like maleic acid, citric acid, oxalic acid, (+)-tartaric acid, and vitamins like ascorbic acid, riboflavin, thiamin pyrophosphate or the provitamin beta-carotene. Hence, in a specific embodiment, the phenolic compound is selected from the group consisting of protocatechuic acid and eugenol, the flavonoid-type polyphenol is selected from the group consisting of anthocyanins, anthocyanidins and a glucoside of quercetin, the organic acid is selected from the group consisting of maleic acid, citric acid, oxalic acid, (+)-tartaric acid, and the one or more of a vitamin and provitamin are selected from the group consisting of ascorbic acid, riboflavin, thiamin pyrophosphate and beta-carotene. Note that some of the above-mentioned acids may be provided by the *Hibiscus sabdariffa* (flower) extract.

Since the appearance and the treatment of the skin are important to many persons, it especially may be desired to use rather all-natural product compounds in the first and the second composition. To this end, the *Hibiscus sabdariffa* extract is preferably used as an active base ingredient in the first and the second composition.

Therefore, in a preferred embodiment the first composition and the second composition in the dermatological kit each independently comprise one or more of, but especially all of the group (a) hibiscus acid (i.e. (+) hydroxycitric acid and/or (+) hydroxycitric acid lactone (2S,3R-dihydroxy-1,2,3-propanetricarboxylic acid lactone)), (b) protocatechuic acid, (c) eugenol, (d) cyaniding-3-sambubioside, (e) cyaniding-3-glucoside, (f) delphinidin-3-sambubioside, (g) delphinidin-3-glucoside, (h) cyanin, (i) malvin, (j) delphinidin, (k) quercetin-3-O-rutinoside, (l) maleic acid, (m) citric acid, (n) oxalic acid, (o) (+)-tartaric acid, (p) ascorbic acid, (q) riboflavin, (r) thiamin pyrophosphate and (s) beta-carotene. The terms "a hibiscus acid" or the "hibiscus acids" especially refers to one or more or a plurality, respectively, of organic acids that can be extracted from the *Hibiscus sabdariffa*. The term "hibiscus acid" may especially refer to the hydroxycitric acid and/or lactone thereof.

Herein, the term "independently" especially indicates that this may apply for the first composition but not for the second composition, or may apply to the second composition but not for the first composition, or may apply to both compositions.

The second (dermatological) composition is specially provided to the brown spot being treated with the first composition to support the peeling process, to stimulate the natural cell renewal in the skin and to protect the sensitive skin from harmful UV radiation. Especially the second composition is provided to boost the exfoliation process. Especially, the second composition also provides moisturizing properties. Buriti oil is the oil extracted from *Mauritia flexuosa* fruit, especially from the pulp of the *Mauritia flexuosa* fruit. The botanical oil contains relative high concentrations of oleic acid, tocopherols and carotenoids, especially beta-carotene, and may be used to treat burns because of its soothing qualities. The oil provides a natural sun protection and may filter and absorb UV rays from the sun.

Therefore in an embodiment the second composition of the (dermatological) kit at least comprises one or more of, but especially all of the group of oleic acid, palmitic acid, palmetoleic acid, stearic acid, linoleic acid, carotenoids, especially beta carotene, a tocopherol, a polyphenol, and a phytosterol.

Especially, in an embodiment the in the (dermatological) kit comprised first composition and second composition comprise a *Hibiscus sabdariffa* extract, especially a *Hibiscus sabdariffa* flower extract and the second composition further comprises the oil extracted from *Mauritia flexuosa*, especially from the *Mauritia flexuosa* fruit. Hence, the first composition and the second composition each independently comprise a *Hibiscus sabdariffa* flower extract and wherein the second composition comprises a *Mauritia flexuosa* fruit extract, especially a *Mauritia flexuosa* fruit oil.

In a specific embodiment the first composition has a *Hibiscus sabdariffa* flower extract concentration, defined as weight ratio relative to the total weight of the first composition, wherein the second composition has a *Hibiscus sabdariffa* flower extract concentration, defined as weight ratio relative to the total weight of the second composition, with weight ratios in the range of 4:1-1:4. Hence, assuming 100 gram first composition comprising 1 gram *Hibiscus sabdariffa* flower extract and 100 gram second composition comprising 0.5 gram *Hibiscus sabdariffa* flower extract, then the ratio (in the kit) is 1:2.

The extracts can be obtained in different ways. In a specific embodiment, the extraction (method) to provide the extracts, be it the *Hibiscus sabdariffa* extract or the *Mauritia flexuosa* extract, are obtainable by a method comprising a water-alcohol extraction. The alcohol may comprise one or more of a C1-4 alcohol, especially at least ethanol.

In yet a further embodiment, the first composition has a hibiscus acid concentration, defined as weight ratio relative to the total weight of the first composition, wherein the second composition has a hibiscus acid concentration, defined as weight ratio relative to the total weight of the second composition, with weight ratios in the range of 4:1-1:4. Above, the ratios of the extract contribution are provided; here the ratios of the hibiscus acid in the compositions are given.

In a specific embodiment, the first composition has a concentration of trichloroacetic acid selected from the range of 1-20 wt. %, such as 5-15 wt. % and a hibiscus acid concentration selected from in the range of 0.02-15 wt. %, such as 0.05-12 wt. %, like especially 0.5-10 wt. %, like 0.5-5 wt. %, such as at least 0.75 wt. % relative to the total weight of the first composition, and the pH is especially in the range of equal to or smaller than 2, such as equal to or smaller than 1, like 0.5-1. Such composition may be most effective. Note that other components may be comprised by the first composition (see also below).

In yet a further specific embodiment, the second composition further comprises a UV filter selected from the group consisting of ethylhexyl methoxycinnamate, ethylhexyl salicylate, diethylamino hydroxybenzoyl hexyl benzoate, and methylene bis-benzotriazolyl tetramethylbuthylphenol, wherein in the second composition a concentration of an oil extracted from the *Mauritia flexuosa* fruit is selected in the range 0.2-10 wt. %, such as especially 1-3 wt. %, a hibiscus acid concentration is selected in the range of 0.02-15 wt. %, such as 0.05-12 wt. %, like especially 0.5-10 wt. %, like 0.5-5 wt. %, such as at least 0.75 wt. %, and a concentration of tocopherol is in the range of 0.05-10 wt. %, such as especially 0.1-4 wt. % relative to the total weight of the first composition, and wherein especially the sun protection factor of the second composition is at least 20, such as at least. Especially, the second composition has a pH in the range of 3-6, such as especially 4-5.

The above-indicated hibiscus acid concentration relates to the total amount of organic acids (that can be available in a *Hibiscus sabdariffa* extract) which are in an embodiment selected from the group consisting of (a) hydroxycitric and/or hydroxycitric acid lactone, (b) garcina acid, (c) pyruvic acid, (d) tartaric acid, (e) salicylic acid, (f) fumaric acid, (g) citric acid, (h) malic acid, (i) formic acid, (j) lactic acid, (k) glycolic acid, (l) ascorbic acid and (m) acetic acid. As indicated above, the first and second composition especially at least comprise (+) hydroxycitric acid (HCA) and/or (+) hydroxycitric acid lactone (2S,3R-dihydroxy-1,2,3-propanetricarboxylic acid lactone). In a specific embodiment, the hibiscus acid comprises one or more of (−) HCA and (+) HCA. The HCA (including lactone) content appears to be in the order of 70% of all organic acids in the *Hibiscus sabdariffa* extract.

Further, alternatively or additionally to the to the *Hibiscus sabdariffa* extract a *Garcinia cambogia* extract may be applied. Other equivalent abstracts may optionally also be used (as alternative or as additive). Hence, the invention also provides a (dermatological) kit comprising a first container comprising a first (dermatological) composition and a second container comprising a second (dermatological) composition (different from the first composition), wherein the first composition comprises trichloroacetic acid (TCA) and an organic acid from a *Garcinia cambogia* extract, especially wherein the first composition comprises trichloroacetic acid and a *Garcinia cambogia* extract, and wherein the second composition also comprises an organic acid from a *Garcinia cambogia* extract, especially such extract, and further a material of *Mauritia flexuosa* origin. Even more especially, the invention provides a (dermatological) kit comprising a first container comprising a first composition and a second container comprising a second composition, different from the first composition, wherein the first composition comprises trichloroacetic acid and an organic acid from a *Garcinia cambogia* extract (or such extract), wherein the second composition comprises a material of *Mauritia flexuosa* origin and an organic acid from a *Garcinia cambogia* extract (or such extract), and wherein the second composition especially has a sun protection factor (SPF) of at least 15, such as at least 20, even more at least 25, such as at least 30, even more at least 50. Herein, the invention is described especially in relation to hibiscus acid. The invention is especially described herein in relation to the kit with hibiscus acid; the embodiments described in relation thereto may also be applicable to an organic acid from a *Garcinia cambogia* extract (or such extract).

The term sun protection factor (SPF) is known in the art. Especially, the sun protection factor is determined according to ISO 24444:2010.

Further, the compositions described herein, especially the (dermatological) compositions comprising *Hibiscus sabdariffa* flower extract and/or Buriti oil, may include other ingredients, not originally from *Hibiscus sabdariffa* and/or the *Mauritia flexuosa* fruit.

For instance, the (first and/or second, especially at least the second) composition may further include one or more excipients. An excipient is especially an inactive substance formulated alongside the active ingredient(s) of a product or medication, for the purpose of bulking-up formulations that contain such active ingredient(s). Excipients may for instance also be indicated as filler or diluent. Excipients may e.g. include one or more of binders, coatings, disintegrates, fillers, flavors, colorants, lubricants, glidants, sorbents, preservatives, sweeteners, etc. The composition may further (also) comprise pentylene glycol. Pentylene glycol is used as moisturizing agent. It is a colorless liquid, very low in odor, that is both water and oil-soluble. Due to its unique molecular properties, including a well separated charge distribution pattern, pentylene glycol performs its moisturizing activity much better than comparable chemicals, i.e. propylene glycol.

The (first and/or second, especially at least the second) composition may further e.g. comprise glycerin. Glycerin (or glycerol) is a polyol compound. It is a colorless, odorless, viscous liquid that is widely used in pharmaceutical formulations. Glycerol has three hydroxyl groups that are responsible for its solubility in water and its hygroscopic nature. The glycerol backbone is central to all lipids known as triglycerides. Glycerol is sweet-tasting and of low toxicity. Glycerol is used (in medical and pharmaceutical and personal care preparations), mainly as a means of improving smoothness, providing lubrication and as a humectant.

The (first and/or second, especially at least the second) composition may further e.g. comprise Pemulen®. The composition may further e.g. comprise one or more of zinc oxide, menthol, bisalol, paraffin, laureth-9, penthylene glycol, Polyglyceryl-3 methylglucose distearate, and citric acid. Pemulen® a polymeric emulsifier which has the capability to absorb oil and water, forming a very stable oil-in-water emulsion. Zinc oxide is a white opaque pigment which prevents bacterial growth and offers UV protection. Menthol may provide a cooling effect, which diverts one's attention away from itching. Due to the cooling effect, the composition, such as when used as spray, may also be effective for the relief of itching effect. Bisalol may be used as a conditioning agent with soothing and anti-irritating properties, accelerating wound healing. Laureth-9 is an emulsifier with anti-itching properties and liquid paraffin can be used as lubricant; both ingredients calm, soften and protect de skin. Penthylene glycol is a moisturizer which facilitates the natural healing process. Polyglyceryl-3 methylglucose distearate may be used as an emulsifier which forms stable emulsions with all common oils and fats. Citric acid is a natural preservative and is used to lower the pH.

The second composition may further comprise one or more of, especially all selected from the group of ethylhexyl methoxycinnamate, ethylhexyl salicylate, diethylamino hydroxybenzoyl hexyl benzoate, and methylene bis-benzotriazolyl tetramethylbuthylphenol. These compounds all offer UV protection and especially may be comprised in the second composition.

Hence, it appears to provide the best results in terms of treatment efficiency when the first composition comprises water, the material of *Hibiscus sabdariffa* origin, such as hybiscus acid or an extract of the *Hibiscus sabdariffa* (comprising hibiscus acid), trichloroacetic acid, and optionally a gelling material such as a gum, especially xanthan gum. Xanthan gum may improve application to the skin. Hence, it also appears to provide the best results in terms of treatment efficiency when the second composition comprises (i) one or more of chelating agent and a gelling agent, especially at least a gelling agent, (ii) a humectant and a stabilizer, especially at least a humectant, (iii) one or more of water and a soothing agent, especially at least water, (iv) a UV filter, (v) one or more of an oil in water emulsifier and an emollient, especially at least an oil in water (O/W) emulsifier, (vi) the material of *Mauritia flexuosa* origin and the material of *Hibiscus sabdariffa* origin, especially at least one or more oils which are known to be contained by the *Mauritia flexuosa* and hibiscus acid, and (vii) optionally one or more other components, such as for instance selected from the group consisting of a preservative, a fragrance, and a pH adjuster.

Herein, the kit is especially explained with reference to such kit comprising both compositions, i.e. at least two containers, each comprising one of the compositions. However, the kit may also include one or more containers with one or more other compositions respectively. For instance, a third container may comprise the substantially the same composition as the second container, but not including the hibiscus acid.

The kit may further include a manual. The manual may include amongst others information on how to apply the first composition. The manual may include amongst others information on how to apply the second composition. When one or more applicators are included in the kit, the manual may also include information on how to apply the one or more applicators. In yet a further aspect, the invention also provides a (dermatological) kit comprising the first container with the first composition or the second container with the second composition, and optionally a manual including information on how to apply the first composition or second composition, respectively.

Hence, in an embodiment the invention also provides a (dermatological) kit comprising a (second) composition comprising a material of *Mauritia flexuosa* origin and a hibiscus acid, wherein the second composition especially has a sun protection factor (SPF) of at least 15. Such kit may optionally also include a manual (for use of the composition). Hence, the invention also provides in an embodiment a (second) composition comprising a material of *Mauritia flexuosa* origin and a hibiscus acid, wherein the second composition especially has a sun protection factor (SPF) of at least 15, such as at least 30.

The material of *Mauritia flexuosa* origin may in an embodiment at least comprise one or more of, but especially all of the group of oleic acid, palmitic acid, palmetoleic acid, stearic acid, linoleic acid, carotenoids, especially beta carotene, a tocopherol, a polyphenol, and a phytosterol. In yet another embodiment, the material of *Mauritia flexuosa* origin comprises a of *Mauritia flexuosa* extract.

The first composition and second composition differ. The difference may especially be in the composition of the ingredients, i.e. different components and/or the same components but different relative contributions (relative weights to the respective compositions). Alternatively or additionally, the first composition and second composition differ (also) with respect to viscosity, with especially the second composition having a higher viscosity than the first composition.

In it is a further aspect of the invention to provide a (dermatological) kit to treat and/or prevent UV (sun) induced hyperpigmentation. In a specific embodiment the (dermatological) kit according to the present invention is provided for use in the treatment and/or prevention of an sun induced skin hyperpigmentation, especially brown spot (solar lentigo), wherein the first composition is used to remove and/or fade the hyperpigmentation and the second composition is used to remove and/or fade the hyperpigmentation and to prevent the re-development of hyperpigmentation.

It is surprisingly found that applying the first composition for initiating the peeling of the skin including the brown spot and in a second stage applying the treating second composition for further treatment, healing, protecting the skin from sun radiation and preventing the brown spot from reappearing leads to better results than using a standard sun milk with the same sun protection factor in the second stage instead of applying the second composition. Especially the healing process is supported by the second composition, whereas reappearance of the brown spot is prevented by the second composition Especially the second composition may comprise a cream. Hence the invention also provides a cream comprising a second composition, wherein the second composition comprises a material of *Mauritia flexuosa* origin and a hibiscus acid, and wherein the second composition has a sun protection factor (SPF) of at least 15, such as alt least 30, such at least 50. Especially, such cream may be provided at a brown spot treated with the first composition, especially to support the exfoliation process, and especially to stimulate regeneration of the skin. Such cream may further provide UV protection and moisturizing properties. Especially, the material of *Mauritia flexuosa* may provide soothing properties to the skin.

In an embodiment of the treatment, an applicator pen device is provided with a topical first composition. The wet tip of the pen applicator is gently and precisely applied against the brown spot. After the application, the wet spot is allowed to dry for 5 minutes to form a dry layer, especially wherein the first composition is allowed to (at least partially) penetrate the skin (the brown spot). Next, the skin is rinsed off with cool water and allowed to dry. Next, the second composition is applied to the treated area. In a period of at least 30 days after the application of the first composition, the peeling takes place gradually. During this period the second composition is applied at least once a day, such as at least twice a day, at the treated area. During this period, the first composition especially may be provided at 5 consecutive days.

The term "substantially" herein, such as in "substantially free" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The devices herein can amongst others be described during operation. As will be clear to the person skilled in the art, the invention is not limited to methods of operation or devices in operation. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage. The invention further pertains to a method or process comprising one or more of the characterizing features described in the description. The various aspects discussed in this patent can be combined in order to provide additional advantages. Furthermore, some of the features can form the basis for one or more divisional applications.

The one or more active ingredients, such as the hibiscus acid and/or the trichloroacetic acid cannot be excluded to have a physical device function; hence, they might have such function. Hence, one or more active ingredients might not produce any chemical reaction or change in the cells of the body and the effect may only physical. Hence, the first composition and/or the second composition have a physical mode of action (function) (unlike e.g. a pharmaceutical, immunological or metabolic active ingredient).

Experimental

The Exfoliating Action of Various Plant Extracts

The exfoliating action of various plant extracts from human skin explants ex vivo is evaluated. Particular attention is paid to the morphology of the stratum corneum. Activity is assessed by examination of the morphology.

*Hibiscus sabdariffa* flower extract is commercially available and is known amongst others as CAS 84775-96-2. This may include 45 wt. % organic acids.

TABLE 1

Products Tested

| Product | Identification | Appearance | Quantity |
|---|---|---|---|
| P1 | Natural Salicylic Acid | White powder | 3 g |
| P2 | Acerola cherry 34 | beige powder | 3 g |
| P3 | Lactic acid | Transparent liquid | 2 mL |
| P4 | glycolic acid | Transparent liquid | 2 mL |
| P5 | Lemon 150-BS_100347 | beige powder | 3 g |
| P6 | Sample TCA-Active 15% | Transparent liquid | 5 mL |
| P7 | Organic acids from *Hibiscus* 50% | beige powder | 3 g |

Preparation of the Products

The product P1 was dissolved to 1% in ethanol/distilled sterile water (2:10) and then diluted to ½ and ¼ in sterile distilled water to obtain solutions at 0.5% and 0.25%.

The products P2 to P7 were solubilized to 1% in sterile distilled water, then diluted to ½ and ¼ in sterile distilled water to obtain solutions at 0.5% and 0.25% water.

Preparation of the Explants 69 explants with a diameter of 11 mm (±1 mm) were prepared from a tummy tuck a Caucasian woman aged 53 (reference P1206-AB53).

The explants were stored in BEM (BIO-EC's Explants Medium) at 37° C. in a humid atmosphere enriched with 5% C02.

The distribution of explants in 23 batched was done as indicated in table 2.

TABLE 2 distribution of explants

| Batch | Treatment | No. explants | Sample |
|---|---|---|---|
| T0 | None | 3 | Day 0 |
| T | None | 3 | DAY 4 |
| P1C1 | Natural Salicylic Acid, 1% | 3 | DAY 4 |
| P1C2 | Natural Salicylic Acid, 0.5% | 3 | DAY 4 |
| P1C3 | Natural Salicylic Acid, 0.25% | 3 | DAY 4 |
| P2C1 | Acerola cherry 34, 1% | 3 | DAY 4 |
| P2C2 | Acerola cherry 34, 0.5% | 3 | DAY 4 |
| P2C3 | Acerola cherry 34, 0.25% | 3 | DAY 4 |
| P3C1 | Lactic Acid, 1% | 3 | DAY 4 |
| P3C2 | Lactic Acid, 0.5% | 3 | DAY 4 |
| P3C3 | Lactic Acid, 0.25% | 3 | DAY 4 |
| P4C1 | Glycolic Acid, 1% | 3 | DAY 4 |
| P4C2 | Glycolic Acid, 0.5% | 3 | DAY 4 |
| P4C3 | Glycolic Acid, 0.25% | 3 | DAY 4 |
| P5C1 | Lemon 150-BS_100347, 1% | 3 | DAY 4 |
| P5C2 | Lemon 150-BS_100347, 0.5% | 3 | DAY 4 |
| P5C3 | Lemon 150-BS_100347, 0.25% | 3 | DAY 4 |
| P6C1 | Sample TCA-Active 15%, 1% | 3 | DAY 4 |
| P6C2 | Sample TCA-Active 15%, 0.5% | 3 | DAY 4 |
| P6C3 | Sample TCA-Active 15%, 0.25% | 3 | DAY 4 |

TABLE 2-continued distribution of explants

| Batch | Treatment | No. explants | Sample |
|---|---|---|---|
| P7C1 | Organic acids from *Hibiscus* 50%, 1% | 3 | DAY 4 |
| P7C2 | Organic acids from *Hibiscus* 50%, 0.5% | 3 | DAY 4 |
| P7C3 | Organic acids from *Hibiscus* 50%, 0.25% | 3 | DAY 4 |

Product Application

The test product is applied topically at a rate of 2 µl per explant, using a spatula to spread, on days 0, 2 and 3. Explants batch T received no treatment except for a renewal of the medium that has been achieved for all items on Day 3

Samples

On day 0, the 3 explants of batch T0 were removed and cut into 2. One portion was fixated in a buffered formalin solution and the second part was frozen at −80° C. At Day 4, the 3 explants of each batch were taken and treated in the same manner.

Treatments Histological

After a fixation of 24 hours in buffered formalin, the samples were dried and soaked in paraffin using an automatic dehydration system, Leica TP 1020. They were embedded in a resin using a coating system Leica EG 1160.

Slices of 5 microns have been produced using a microtome type Minot Leica RM 2125 and mounted on microscope slides type histological SuperFrost®.

Microscopic observations were performed by optical microscopy, using a Leica Orthoplan microscope and an Olympus BX43. The shots were made with an Olympus DP72 camera and Cell ^ D software.

Review of Overall Morphology

Paraffin sections were stained with Masson's trichrome stain, Goldner variant. Microscopic examination was carried out to assess the general morphology of the dermal and epidermal structures.

Particular attention was paid to the morphology of the Stratum Corneum.

Results

General Morphology

Control Batch at Day 0 (T0): The stratum corneum is thin, slightly to moderately foliated, distinct keratinized surface and base. It has many cell layers and appeared normal. The epidermis has 4-5 cell layers with good morphology. The relief of the dermal-epidermal junction is clear. The papillary dermis shows moderately thick collagen bundles forming a dense network. The morphology of dermal cells is good.

Control Batch at Day 4 (TJ4): The stratum corneum is moderately thick, fairly well laminated, moderately keratinized surface and clearly at its base. It has many cell layers and appeared normal. The epidermis has 4-5 cell layers with a fairly good morphology. The relief of the dermal-epidermal junction is clear. The papillary dermis shows moderately thick collagen bundles forming a dense network. The morphology of dermal cells is good.

Batch P1 1%, at Day 4 (P1C1J4): The stratum corneum is moderately thick, fairly well laminated, moderately keratinized surface and distinctly at its base. It has quite a number of cell layers with a light exfoliation of the upper layers. The dermal and epidermal morphology is similar to that observed on TJ4.

Batch P1 0.5%, at Day 4 (P1C2J4): The stratum corneum is moderately thick, fairly well laminated, moderately keratinized surface and clearly at its base. It has many cell layers and appeared normal. The dermal and epidermal morphology is similar to that observed on TJ4.

Batch P1 0.25%, at Day 4 (P1C3J4): The stratum corneum is moderately thick, fairly well laminated, moderately keratinized surface and clearly at its base. It has many cell layers and appeared normal. The dermal and epidermal morphology is similar to that observed on TJ4.

Batch P2 1%, at Day 4 (P2C1J4): The stratum corneum is moderately thick, fairly well laminated, moderately keratinized surface and clearly at its base. It has many cell layers with a very light exfoliation of the upper layers. The dermal and epidermal morphology is similar to that observed on TJ4.

Batch P2 0.5%, at Day 4 (P2C2J4): The stratum corneum is moderately thick, fairly well laminated, moderately keratinized surface and clearly at its base. It has many cell layers and appeared normal. The dermal and epidermal morphology is similar to that observed on TJ4.

Batch P2 0.25%, at Day 4 (P2C3J4): The stratum corneum is moderately thick, fairly well laminated, moderately keratinized surface and clearly at its base. It has many cell layers and appeared normal. The dermal and epidermal morphology is similar to that observed on TJ4.

Batch P3 1%, at Day 4 (P3C1J4): The stratum corneum is moderately thick, fairly well laminated, moderately keratinized surface and clearly at its base. It has quite a number of cell layers with a light exfoliation of the upper layers. The dermal and epidermal morphology is similar to that observed on TJ4.

Batch P3 0.5%, at Day 4 (P3C2J4): The stratum corneum is moderately thick, fairly well laminated, moderately keratinized surface and clearly at its base. It has many cell layers with a very light exfoliation of the upper layers.

Batch P3 0.25%, v (P3C3J4): The stratum corneum is moderately thick, moderately to quite well laminated, moderately keratinized surface and clearly at its base. It has many cell layers and appeared normal. The dermal and epidermal morphology is similar to that observed on TJ4.

Batch P4 1%, at Day 4 (P4C1J4): The stratum corneum is moderately thick, moderately to quite well laminated, moderately keratinized surface and clearly at its base. It has many cell layers with a light and irregular exfoliation of the upper layers. The dermal and epidermal morphology is similar to that observed on TJ4.

Batch P4, 0.5%, at Day 4 (P4C2J4): The stratum corneum is moderately thick, moderately foliated, moderately keratinized surface and clearly at its base. It has many cell layers with a very light and irregular exfoliation of the upper layers. The dermal and epidermal morphology is similar to that observed on TJ4.

Batch P4, 0.25%, at Day 4 (P4C3J4): The stratum corneum is moderately thick, fairly well laminated, moderately keratinized surface and clearly at its base. It has many cell layers and appeared normal. The dermal and epidermal morphology is similar to that observed on TJ4.

Batch P5 1%, at Day 4 (P5C1J4): The stratum corneum is moderately thick, laminated pretty well, clearly keratinized surface and at its base. It has many cell layers and appeared normal. The dermal and epidermal morphology is similar to that observed on TJ4.

Batch P5 0.5%, at Day 4 (P5C2J4): The stratum corneum is moderately thick, laminated pretty well, clearly keratinized surface and at its base. It has many cell layers and appeared normal. The dermal and epidermal morphology is similar to that observed on TJ4.

Batch P5 0.25%, at Day 4 (P5C3J4): The stratum corneum is moderately thick, fairly well laminated, moderately keratinized surface and clearly at its base. It has many cell layers and appeared normal. The dermal and epidermal morphology is similar to that observed on TJ4.

Batch P6 1%, at Day 4 (P6C1J4): The stratum corneum is moderately thick, laminated pretty well, clearly keratinized surface and at its base. It has a moderate number cell layers with moderate exfoliation of the upper layers. The dermal and epidermal morphology is similar to that observed on TJ4.

Batch P6 0.5%, at Day 4 (P6C2J4): The stratum corneum is moderately thick, laminated pretty well, clearly keratinized surface and at its base. It has quite a number of cell layers with a light and irregular exfoliation of the upper layers. The dermal and epidermal morphology is similar to that observed on TJ4.

Batch P6 a 0.25%, at Day 4 (P6C3J4): The stratum corneum is moderately thick, laminated pretty well, clearly keratinized surface and at its base. It has many cell layers and appeared normal. The dermal and epidermal morphology is similar to that observed on TJ4.

Batch P7 1%, at Day 4 (P7C1J4): The stratum corneum is little to moderately thick, laminated pretty well, moderately keratinized surface and clearly at its base. It has a moderate number cell layers with moderate exfoliation of the upper layers. The dermal and epidermal morphology is similar to that observed on TJ4.

Batch P7 0.5%, at Day 4 (P7C2J4): The stratum corneum is moderately thick, laminated pretty well, clearly keratinized surface and at its base. It has quite a number of cell layers with a very light exfoliation higher layers.

The dermal and epidermal morphology is similar to that observed on TJ4.

Batch P7 à 0.25%, at Day 4 (P7C3J4): The stratum corneum is moderately thick, laminated pretty well, clearly keratinized surface and at its base. It has many cell layers with a very light exfoliation of the upper layers. The dermal and epidermal morphology is similar to that observed on TJ4.

Discussion

General Morphology

At day 0, the stratum corneum is thin, slightly to moderately foliated, well keratinized at the surface and at its base. It has many cell layers and appeared normal. The epidermis has 4-5 cell layers with good morphology. The relief of the dermal-epidermal junction is clear. The papillary dermis shows moderately thick collagen bundles forming a dense network. The morphology of dermal cells is good. On Day 4, the stratum corneum is moderately thick, fairly well laminated, moderately keratinized at the surface and distinctly at its base. It has many cell layers and appeared normal. The dermal and epidermal morphology is similar to that observed on TJ4. For all the treated groups, the epidermal and dermal morphology is similar to that observed on TJ4. The morphology of the stratum corneum exfoliation is more or less pronounced and is described below.

Product P1 slightly reduced the number of cell layers of SC and has a light exfoliation to the concentration 1% (C1). It does not present a significant exfoliating activity at concentrations 0.5% and 0.25% (C2 and C3). Product P2 shows a slight exfoliation at the 1% concentration (C1). It shows no significant activity exfoliating at other concentrations. Product P3 slightly reduced the number of cell layers of the SC and has a light exfoliation at the concentration of 1% (C1). It has a very light exfoliation at the concentration of 0.5% (C2) and no appreciable exfoliating activity at concentration 0.25% (C3). Product P4 has a slight irregular exfoliation at 1% concentration (C1). It has a very light exfoliation at the 0.5% concentration (C2) and no appreciable exfoliating activity at 0.25% concentration (C3). Product P5 does not present a significant exfoliating activity at the concentrations tested. Product P6 shows a moderately reduced number of cell layers in the SC and has moderate exfoliation at 1% concentration (C1). The number of cell layers are slightly reduced and an uneven exfoliation is shown at 0.5% concentration (C2) and no significant activity in the exfoliation is shown at 0.25% concentration (C3). Product P7 moderately reduced the number of cell layers of the SC and has moderate exfoliation at 1% concentration (C1). The number of cell layers are slightly reduced and an very low exfoliation is shown at the 0.5% concentration (C2) and a very slight exfoliation activity at 0.25% concentration (C3) is shown.

Using the given operating conditions and compared to the control group at Day 4 (TJ) the results are visualized in the Table 3. As can be seen from Table 3, TCA (P6) and hibiscus acids (P7) show the best exfoliating activity, especially samples of 1% concentration.

TABLE 3

Exfoliating activity; n.a. = no significant exfoliating activity detected at day 4.

| Test | Result |
| --- | --- |
| P1C1 | 4 |
| P1C2 | n.a. |
| P1C3 | n.a. |
| P2C1 | 2 |
| P2C2 | n.a. |
| P2C3 | n.a. |
| P3C1 | 4 |
| P3C2 | 2 |
| P3C3 | n.a. |
| P4C1 | 4 |
| P4C2 | 3 |
| P4C3 | n.a. |
| P5C1 | n.a. |
| P5C2 | n.a. |
| P5C3 | n.a. |
| P6C1 | 6 |
| P6C2 | 4 |
| P6C3 | n.a. |
| P7C1 | 6 |
| P7C2 | 4 |
| P7C3 | 2 |

Below, an embodiment of the two compositions and their applications are given. It refers to a kit comprising the first composition comprised by an applicator pen and the second composition as cream comprised in a container.

Brown Spot Treatment Pen and Prevention Cream

Brown spot pen is a medical device for the local treatment of hyperpigmentation known as age spots. Brown spots are caused by an increase of pigmentation of the skin under the influence of the sunlight. The skin aging and frequently exposed to sunlight has a tendency to become blotchy. The ingredients of brown spot pen induces the discoloration of the skin to fade away the brown spot by regenerating the skin for a new uniform appearance. The pen allows a quick, easy and accurate treatment of the spot.

Brown spot pen can be used for any type of skin with brown spots caused by sunlight. As far as know, brown spot treatment can be used during pregnancy and lactation.

The skin is a living organ made up of millions of cells. Everyday thousands of cells die, fall off and are replaced by new cells from below. Unfortunately, as we age, this becomes slower and more haphazard process, making your skin unable to shed dark blotches and sun damage.

Brown spots also called liver spots are blemishes on the skin associated with aging and exposure to the sun. They occur mainly on sun-exposed parts of the body such as the face, neck, décolleté, upper back, arms, hands and feet. They range in color from light brown to dark brown, nonpainful, usually uniform in color, have smooth border and remain stable in appearance. They should be differentiated from freckles, moles and melanoma (skin cancer).

Brown spot pen delivers locally the ingredients which create an injury of the skin with the goal of stimulating new skin growth and improving surface texture and appearance.

Some skin problems may be deeper than others. Depending of the depth of the brown spot, it is possible that more than one peel may be required to achieve the best results.

Before applying the product, it is desirable to wash the skin thoroughly. The use of a cream or lotion is not recommended, as it may leave residues.

After the application, it is recommended to wait a few minutes, such as 5 minutes for the first layer to dry. If the brown spot is dark, optionally a second layer after that the first layer is dried may be applied. After the application, it is recommended to wait a few minutes, such as 5 minutes for the second layer to dry. Thereafter, it is recommended to rinse off with cool water and dry the skin gently once the first or second layer is dried. It is further recommended to apply thereafter the prevention cream on the treated area.

The product will dry out the top layers of skin cells. The user might experience stinging, itching, burning, slight pain, tightness and scabbing of the treated area which will diminish as the skin return to its "normal". The skin may peel off over a period of several days. When the old skin has peeled off, it exposes a new layer of undamaged skin with a smoother texture and more even color. It is recommended not to use scrubs or abrasive products on the treated area.

It is recommended to wash the treated area very gently with a mild cleanser twice a day. Especially it is desirable to prevent the skin to dry out.

During this peel off period, it is recommended to use the second composition, here the brown spot prevention cream every day to protect your skin from the rays of the sun. The user should use it even if the user is out only for 5 minutes, or if it is cloudy, or if the user wears a hat. The user should use the brown spot prevention cream or other type of second composition continuously for 1 month after the first application of the brown spot treatment pen, or other way of applying the first composition.

Although one application can significantly fade away the brown spot, the user might need additional applications for achieving best results as some brown spots are deeper than others. For the next use, the user should wait until the treated skin returns to "normal". This might take 2-4 weeks.

Efficacy Study on the Brown Spot Treatment Pen

An efficacy study in order to clinically evaluate the efficacy and safety of the Brown Spot Treatment Pen in combination with the Brown Spot Prevention Cream, a cream comprising Buriti oil and hibiscus acids with an SPF 30 in order to protect the treated skin is performed. The secondary aim of the study was to evaluate the efficacy and safety of two different concentrations of TCA in the Treatment Pen: 10% and 15%, with the same amount of hibiscus acid HA). The amount of TCA in the gel in the Treatment Pen, is calculated using the weight in volume (W/V) method. When a 10% strength is claimed, this means that the preparation contains 10 grams of TCA crystals in 100 mL of solution.

In total 40 subjects were enrolled and 36 subjects (33 females and 3 males), aged 29 to 89 years (mean 55), participated from September 2014 to January 2015 and completed the study. Four subjects did not show up for follow up visits. The 36 subjects were divided in two groups. One group received the treatment with 10% of TCA and the other one received 15% of TCA, applied for five consecutive days associated with the protective cream applied for 30 days. Treatment of the brown spots for both TCA concentrations was done according standard treatment protocol: The skin is first washed with a cleanser. Successively the gel (comprising composition 1) from the treatment pen is applied precisely on the brown spot. After 5 minutes the treated skin is washed with water. Successively the skin at the location of the brown spot is provided with the treatment cream (comprising composition 2). Treatment with the treatment pen is provided for 5 consecutive days. The treatment cream is applied daily for the period of 30 days.

Clinical improvement was graded according to a standardized scale of skin colors by professional and highly experienced skin specialists at Day 0, Day 5, Day 15 and Day 30, and pictures were taken as well. Subjects filled in a diary every day for the first five days, and then at Day 7, Day 15, Day 20 and Day 30. Each subject answered a satisfactory questionnaire once the study was completed. A total of 46 brown spots were treated with a composition with 10% of TCA and 21 spots were treated with 15% of TCA. For both concentrations, after 30 days, disappearance of the brown spot was achieved in 17 spots out of the 46 treated spots (37%).

Overall, the spots became darker (brownish/pinkish) by forming a thin crust, until day 4. Crusts fell off around day 7/day 15, leaving a fresh renewed skin around day 20/day 30. For both concentrations, after 30 days, disappearance of the brown spot was achieved in 17 spots out of the 46 treated spots (37%). For the treatment with 10% of TCA, 11 spots out of 25 treated (44%) disappeared For the treatment of 15% of TCA, 6 spots out of 21 treated (29%) disappeared. The other 28 spots became lightened by the treatment (61%). The pigment of one spot did not change as it was probably wrongly diagnosed as a solar lentigine. Results are given in the table below:

TABLE 4

Number of spots responding to treatment.

|  | Day 15 | | Day 30 | |
| --- | --- | --- | --- | --- |
|  | Disappeared | Lightened | disappeared | Lightened |
| Response to 10% of TCA out of 25 treated spots | 3 (12%) | 20 (80%) | 11 (44%) | 12 (48%) |
| Response to 15% of TCA out of 21 treated spots | 0 (0%) | 16 (76%) | 6 (29%) | 15 (71%) |

During the Efficacy Study performed on Brown Spot Treatment Pen in combination with the protective Prevention Cream, no serious adverse effects were reported. The very common effects observed during treatment were frosting for few minutes after TCA application. The common adverse effects observed only during treatment were burning, stinging, itching, redness or irritation on the treated spot from 2 to 5 minutes after TCA application, see table below. Subjects with the treatment with 10% of TCA experienced more common adverse effects such as burning, stinging and redness than the subjects with the treatment with 15% of TCA. This sensitiveness would be due to lower pigmentation rate of spots included in the group of 10% of TCA. The temporary hypopigmentation observed at Day 30 was more dominant in subject with 15% of TCA. This could be explained by deeper skin damage induced by the treatment with 15% of TCA. Indeed, the deeper the damage is in skin layers, the longer healing takes. Uncommon adverse effects occurred in subjects treated with 15% of TCA, such as itching at day 7 in one subject, swollen vein after one application in one subject, bleeding after cleaning the treated spot at day 5 and slightly swollen treated spot at day 2 in one subject. The subject who experienced swollen vein after one application of the pen, immediately ceased the treatment. The relation between this adverse effect and the treatment has not been established.

TABLE 5

Number of subjects who experienced common adverse effects during the efficacy study out of 21 subjects for TCA 10% and 18 subjects for TCA 15%.

|  | Subjects treated with TCA 10% | Subjects treated with TCA 15% |
| --- | --- | --- |
| Burning sensation after application | 19 | 11 |
| Stinging after application | 19 | 13 |
| Itching after application | 9 | 8 |
| Redness/irritation after application | 15 | 7 |
| Hypopigmentation at Day 30 | 13 | 12 |

CONCLUSION

The results demonstrate that the Brown Spot Treatment and Prevention Kit is an efficient and safe treatment of solar lentigines. After one treatment (application of the pen for 5 consecutive days and the cream for 30 days), both concentrations of 10% and 15% induce a significant partial or complete disappearance of brown spots. However, the comparison of safety of both concentrations indicates that the treatment with 10% of TCA is safer than 15% of TCA for the use of the Brown Spot Kit in Self-Care.

Mechanism of Action

The Brown Spot Treatment Pen based on TCA and hibiscus acids comprising alpha hydroxyl acids (AHAs), induces peeling of the skin by destroying the epidermis and partial dermis through keratocoagulation and protein precipitation. A few minutes after application on solar lentigine, frosting will occur. By applying the gel once a day for 5 consecutive days, the Active Medical Ingredients precipitate the keratinocytes of the treated spot until reaching the superficial layer of the dermis. Experimental results indicated that a crust commonly formed until Day 5. This is an indicator that the upper layers of treated skin are injured. The crust fell off around day 7/day 15, revealing a renewed skin around day 20/day 30. Damaging the skin automatically stimulates the renewal process of the skin. Thus, new healthy skin cells will be produced while the old damaged hyperpigmented skin cells will peel off. Unless over-exposed to UV light during the skin renewal process, the new regenerated skin will appear as new without hyperpigmentation. Thirty days after the first treatment application, the skin may appear as a pink scar. This hypopigmentation occurs with any chemical peel since the epidermis and dermis cells containing melanin pigments have been removed and new melanin pigments must be formed. However, this secondary hypopigmentation is transient as new melanin is continually formed.

It is suggested that chemical peeling with TCA, after exfoliation, induces collagen formation and leads to a thicker skin and better organization of the elastic fibers in the dermis. In the aging skin, known for its 'thinness' and loss of elasticity, these effects contribute to the rejuvenation of the skin, which has also been shown in clinical studies. Consequently, in addition to removing solar lentigines, TCA/hibiscus acid peeling induces skin rejuvenation and improves its elasticity. In addition to TCA, HAs weaken the tight junction (protein) bonds between cells in the outer, 'dead' layer of skin, which speeds up the normal shedding process of dead skin. The HAs reduce the calcium ion concentration in the epidermis and remove calcium ions from the cell adhesions by chelation. This causes a loss of calcium ions from the cadherins of the desmosomes and adherens junctions, from the tight junctions, and possibly also from other divalent metallic cation-dependent cell adhesion molecules. The cell adhesions are thereby disrupted, resulting in desquamation of superficial skin layer. HAs will then help the exfoliation of dead skin cells generated by TCA.

The invention claimed is:

1. A dermatological kit comprising:
a first container comprising a first composition which comprises trichloroacetic acid and hibiscus acid, and
a second container comprising a second composition, different from the first composition, wherein the second composition has a sun protection factor (SPF) of at least 15 and comprises a *Mauritia flexuosa* extract and hibiscus acid, and wherein
each of the first and second compositions is a topical composition comprising a cream, a foam, a gel, a lotion, an ointment or a paste.

2. The dermatological kit according to claim 1, wherein the first composition and the second composition each independently comprise a phenolic compound, a flavonoid-type polyphenol compound, an organic acid, and one or more of a vitamin and provitamin, wherein the phenolic compound is selected from the group consisting of protocatechuic acid and eugenol, wherein the flavonoid-type polyphenol is selected from the group consisting of anthocyanins, anthocyanidins and a glucoside of quercetin, wherein
the organic acid is selected from the group consisting of maleic acid, citric acid, oxalic acid, (+)-tartaric acid, and wherein
the one or more of a vitamin and provitamin are selected from the group consisting of ascorbic acid, riboflavin, thiamin pyrophosphate and beta-carotene.

3. The dermatological kit according to claim 1, wherein the first composition and the second composition each independently comprise hydroxycitric and/or hydroxycitric acid lactone, eugenol, cyaniding-3-sambubioside, cyaniding-3-glucoside, delphinidin-3-sambubioside, delphinidin-3-glucoside, cyanin, malvin, delphinidin, quercitin-3-O-rutinoside, maleic acid, citric acid, oxalic acid, (+)-tartaric acid, ascorbic acid, riboflavin, thiamin pyrophosphate and beta-carotene.

4. The dermatological kit according to claim 1, wherein the second composition comprises at least one selected component from the group consisting of oleic acid, palmitic acid, palmetoleic acid, stearic acid, linoleic acid and a carotenoid.

5. The dermatological kit according to claim 1, wherein the first composition and the second composition each independently comprise a *Hibiscus sabdariffa* flower extract and wherein the second composition comprises a *Mauritia flexuosa* fruit extract.

6. The dermatological kit according to claim 5, wherein the extracts are residues of a water-alcohol extraction.

7. The dermatological kit according to claim 1, wherein
the first composition has a hibiscus acid concentration, defined as a weight ratio relative to the total weight of the first composition, and wherein
the second composition has a hibiscus acid concentration, defined as a weight ratio relative to the total weight of the second composition, and wherein
each of the weight ratios of the first and second compositions is in a range of 4:1-1:4.

8. The dermatological kit according to claim 1, wherein the first composition has a concentration of trichloroacetic acid in a range of 5-15 wt. % and a concentration of organic acids that can be extracted from *Hibiscus sabdariffa* which is in a range of 0.05-12 wt. % relative to the total weight of the first composition, and wherein the first composition has a pH which is in a range of equal to or smaller than 2.

9. The dermatological kit according to claim 1, wherein
the second composition further comprises a UV filter selected from the group consisting of ethylhexyl methoxycinnamate, ethylhexyl salicylate, diethylamino hydroxybenzoyl hexyl benzoate, and methylene bis-benzotriazolyl tetramethylbuthylphenol, and wherein
the second composition has a concentration of an oil extracted from the *Mauritia flexuosa* fruit which is in a range 1-3 wt. % and a concentration of organic acids that can be extracted from *Hibiscus sabdariffa* which is in a range 0.05-12 wt. %, and wherein
the first composition has a concentration of tocopherol which is in a range of 0.1-4 wt. % relative to the total weight of the first composition, and wherein
the second composition has a sun protection factor (SPF) which is at least 20 and a pH which is in a range of 4-5.

10. The dermatological kit according to claim 1, wherein the first composition comprises a gel.

11. The dermatological kit according to claim 1, comprising a first applicator comprising the first composition, or a second applicator comprising the second composition, or both the first applicator comprising the first composition and the second applicator comprising the second composition.

12. The dermatological kit according to claim 11, wherein the first applicator comprises a spray or an applicator pen.

13. The dermatological kit according to claim 1, wherein the kit is for treatment and/or prevention of a sun induced skin hyperpigmentation, wherein the first composition is effective to remove and/or fade the hyperpigmentation and the second composition is effective to remove and/or fade the hyperpigmentation and to prevent the re-development of hyperpigmentation.

14. The dermatological kit according to claim 1, wherein the kit is for the prevention of a sun induced skin hyperpigmentation, wherein the second composition is effective to protect the skin from UV-A and UV-B radiation.

15. The dermatological kit according to claim 1, wherein the second composition comprises at least one carotenoid selected from the group consisting of beta carotene, tocopherols, polyphenols and phytosterols.

16. The dermatological kit according to claim 5, wherein the second composition comprises a *Mauritia flexuosa* fruit oil.

17. The dermatological kit according to claim 13, wherein the skin hyperpigmentation comprises brown spot (solar lentigo).

18. The dermatological kit according to claim 14, wherein the skin hyperpigmentation comprises brown spot (solar lentigo).

19. The dermatological kit according to claim 1, wherein the *Mauritia flexuosa* extract is Buriti oil.

20. A method of treating a brown spot (solar lentigo), the method comprising:
   (i) providing the kit according to claim 1;
   (ii) applying the first composition of the kit on the brown spot;
   (iii) applying the second composition of the kit to the brown spot; and
   (iv) repeating step (iii), wherein
   the first composition is applied on a first day, and thereafter the second composition is applied on a daily basis during at least two weeks.

* * * * *